United States Patent [19]

Galbraith

[11] Patent Number: 4,679,560
[45] Date of Patent: Jul. 14, 1987

[54] WIDE BAND INDUCTIVE TRANSDERMAL POWER AND DATA LINK

[75] Inventor: Douglas C. Galbraith, Stanford, Calif.

[73] Assignee: Board of Trustees of the Leland Stanford Junior University, Stanford, Calif.

[21] Appl. No.: 719,232

[22] Filed: Apr. 2, 1985

[51] Int. Cl.$^4$ ............................................... A61N 1/00
[52] U.S. Cl. .................................. 128/419 R; 128/903
[58] Field of Search ............ 128/419 C, 419 E, 419 P, 128/419 PC, 419 PS, 419 PT, 419 R, 903

[56] References Cited

U.S. PATENT DOCUMENTS 3,195,540  7/1965  Waller ........................... 128/419 PG
3,796,221  3/1974  Hagfors ............................ 128/419 C
4,441,210  4/1984  Hochmair et al. .................. 128/903

Primary Examiner—William E. Kamm
Attorney, Agent, or Firm—Flehr, Hohbach, Test, Albritton & Herbert

[57] ABSTRACT

The present invention utilizes a pair of coils, one beneath the skin and one outside the skin, each connected to a capacitor. The values of the capacitor and coil inductance are selected to provide a stagger-tuned link. That is, the values of the components are selected to place the pole of one filter above the operating frequency, and the pole of the other filter below the operating frequency of the link. The poles will move as the coupling coefficient changes, desensitizing the link to the coupling so that the coils can be misaligned in any manner with little effect on the output.

A fully active driver or class D amplifier is preferably utilized to effectively drive the link with a square wave signal. This signal can be modulated to convey data information to the implanted receiver coil beneath the skin.

14 Claims, 8 Drawing Figures

FOUR COMBINATIONS OF THE STAGGER-TUNED LINK

RELATIVE COIL ALIGNMENTS & POSITIONS
(A) VERTICAL SEPARTION
(B) LATERAL MISALIGNMENT
(C) ANGULAR MISALIGNMENT
(D) GENERAL MISALIGNMENT

FIG__1

FOUR COMBINATIONS OF THE STAGGER-TUNED LINK

*FIG_2*

COUPLING COMPENSATED LINK VOLTAGE GAIN EXAMPLE

*FIG_3A*

FIG_3B

FIG_3C

LINK VOLTAGE GAIN VERSUS COUPLING AND LOAD AT 20MHz

FIG_4

FIG_5

FIG.—6

WIDE BAND INDUCTIVE TRANSDERMAL POWER AND DATA LINK

The present invention is directed generally to the field of medical electronics, and more particularly to a method and apparatus for conveying power and data through the skin of a subject without breaking the skin.

With the increase in use of implanted electronic devices beneath human skin, it has been increasingly desirable to be able to convey power and/or data to the implanted device without puncturing the skin. A typical approach previously followed was to use a percutaneous plug which could deliver power, but must break the skin to reach the stimulator. Breaching the skin provides a potential path for infection to enter, risking the safety of the individual as well as the implant. Another alternative is to implant a battery. Unfortunately, many applications require more amp hours than a battery can provide without frequenc reimplantation.

The use of an inductive link has neither of these limitations since it leaves the skin intact and can draw from an outside power source. For medical applications, an inductive link is usually composed of two pancake shaped coils, one implanted in the body and one outside the body. These coils form a transformer through which energy can be sent. Inductive links are already used to deliver power and information into implanted stimulators. Examples of this can be found in the Ph.D. Dissertation of M. Soma, "Design and Fabrication of an Implantable Multi-channel Neural Stimulator" Ph.D. Dissertation June, 1980; the Ph.D. Dissertation of T. Gheewala, "A CMOS Implantable Auditory Prosthesis Using Integrated Circuit Technology," Stanford University, March 1976, and the article by E. S. Hochmair, IEEE Transactions on Biomedical Engineering, Vol.BME-31, No.2, pp. 177–186, February 1984, entitled, "System Optimization for Improved Accuracy in Transcutaneous Signal and Power Transmission."

However, inductive links as considered in these prior efforts have their own set of difficulties. In the past, these links have had problems providing efficiency, bandwidth, and insensitivity to misalignment.

It is an objective of the present invention to provide a new and improved inductive link.

It is another objective of the present invention to provide such a link whose gain is relatively insensitive to coupling variations between the coils which occur with relative movement between the coils.

Yet another objective of the present invention is to provide an inductive link which has a relatively wide bandwidth.

Efficiency is one of the major problems to be attacked in designing such coupling systems. Efficiency is a problem because the freedom of the implanted person is limited by the portability of the transmitter power source. If the transdermal link is inefficient, an implant of even modest power demand may require a large amount of power to the transmitter. If the system requires an excessive amount of power, the individual must carry a large battery pack. For example, the systems described in the above-referenced Ph.D. theses required a battery pack about the size of a brick which needed recharging every eight hours.

Therefore, it is an objective of the present invention to provide a system which is small and efficient enough for a person to wear freely and use in everyday activities.

Figure 1:
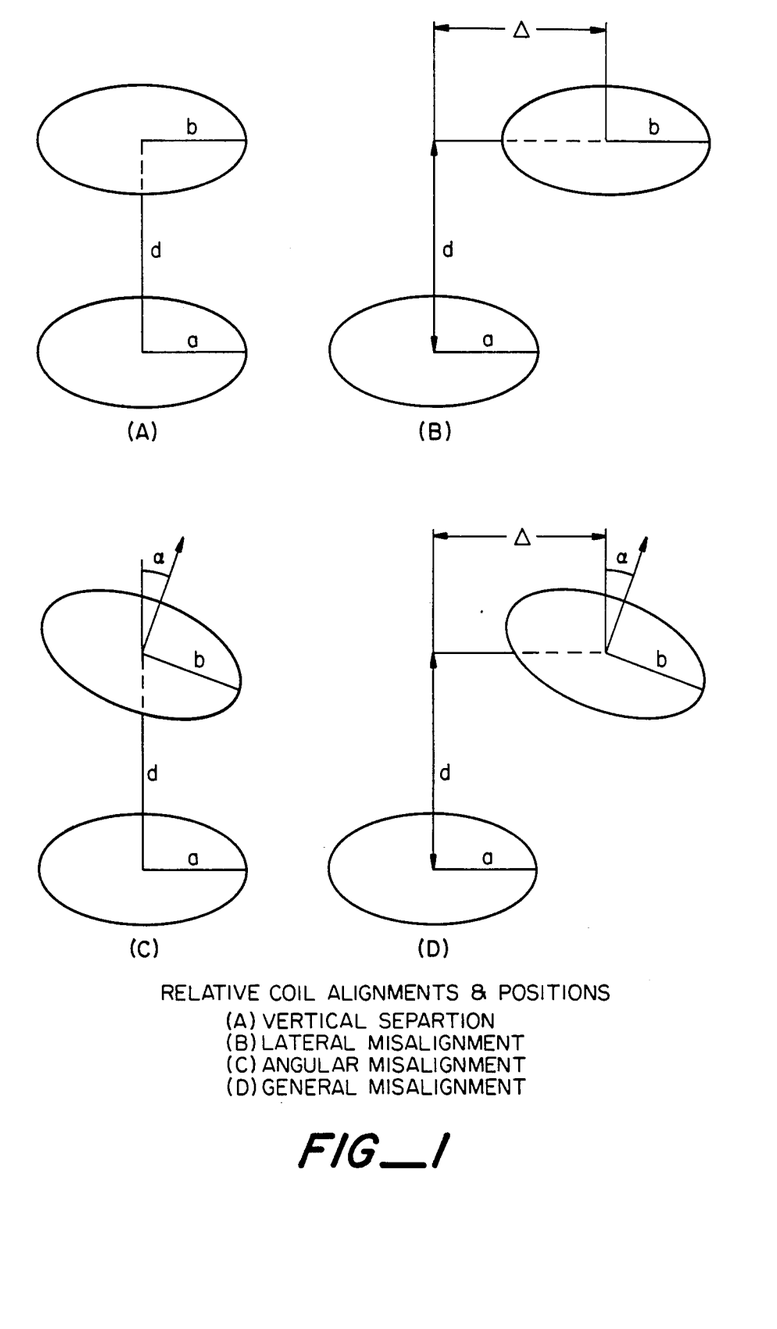
FIG. 1 illustrates the various coil misalignment dealt with by the present invention.

Inductive links have been inefficient because designs to compensate for coil misalignment have been inefficient. The coils can move relative to one another as shown in FIG. 1. As they move, their gain (voltage gain, current gain, transconductance gain, or transimpedance gain, depending on the input and output circuitry) changes, since their coupling depends on their relative positions. Many applications require a stable internal power supply, and therefore, must regulate the output of the receiver coil.

If the gain variation is too large, then most of the received power is not used in the stimulator, but wasted in the regulator coupled to the receiving coil.

The most commonly used approach to solving this problem, called the geometric approach, sacrifices the coupling magnitude in exchange for reduction in the coupling variation. It uses an external coil which is larger than the implanted coil. As long as the small coil remains within the perimeter of the larger coil, both coils will share roughly the same number of flux lines, and the coupling will remain fairly constant. The coils can move laterally and even tilt somewhat with only a minor effect on their gain. This approach is adopted in one or more of the above references.

Unfortunately, in addition to being inefficient, the geometric approach is still sensitive to changes in coil separation; for a small separation (near field), the coupling drops proportionally with separation. If the coil separation doubles, then the gain is cut in half. This approach, therefore, only partially desensitizes the link gain to the coil's position.

Secondly, in exchange for partially controlling the gain, the geometric approach sacrifices the magnitude of the coupling, which raises the losses in the primary coil. Since these coils share fewer flux lines than two equally sized coils, their typical coupling coefficient is lower than their equally sized counterparts. In fact, their coupling is much lower since their shared area diminishes as the square of the lateral misalignment tolerance, i.e., shared area $=\pi$(larger radius-alignment tolerance)$^2$. Lower coupling requires a higher current in the primary coil to provide the same output from the receiver coil; and higher current wastes more power due to the $I^2R$ losses of the transmitter coil.

The earlier links also had another problem, i.e., poor bandwidth. These links were usually single tuned (transmitter coil only) or doubled tuned (both coils) to the carrier frequency so that they could be driven by a semi-passive RF transmitter (Class C, for example) for higher efficiency. Semi-passive transmitters need a high Q tuned circuit to operate efficiently. Unfortunately, the higher the Q, the smaller the band width. The previous Stanford stimulators used a separate ultrasonic data link to obtain a wide band data path, but that link proved much less tolerant to misalignment than the inductive link, and unreliable in use due to acoustic impedance mismatches. Clearly, an efficient wide band power and data link would solve some difficult problems.

In summary, the new approach described in the present invention utilizes a pair of coils, one beneath the skin and one outside the skin, each connected to a capacitor.

The values of the capacitor and coil inductance are selected to provide a stagger-tuned link. That is, the values of the components are selected to place the pole of one filter above the operating frequency, and the pole of the other filter below the operating frequency of the link. The poles will move as the coupling coefficient changes, desensitizing the link to the coupling so that the coils can be misaligned in any manner with little effect on the output.

The present invention includes a number of approaches which differ from obvious uses of stagger tuning or any prior art approaches. The problem is that when the coils move, the coupling coefficient changes and so does the ratio of input to output. The present invention applies stagger tuning to desensitize the link going into the coupling coefficient rather than broaden the band width as is normally done in stagger-tuned filters.

Secondly, the gain is stabilized due to an approach which takes into account and relies on the interaction of two components; typically, gain is stabilized by isolating components from affecting one another.

In a further departure from the approaches of the prior art, a fully active driver or class D amplifier is preferably utilized to effectively drive the link with a square wave signal. This signal can be modulated to convey data information to the implanted receiver coil beneath the skin.

Other advantages of the present invention will become apparent from the following detailed disclosure given with reference to the accompanying drawings wherein:

FIG. 2E is a block diagram of a preferred form of the invention.

The "Voltage Driven:Voltage Out" link of FIG. 2A will illustrate the approach of the present invention to gain control. The voltage gain across an untuned or singly tuned two-coil system varies linearly with the coupling coefficient (assuming the load resistance is large compared to the coil reactance), so if the coupling increases by a factor of three, it will cause the voltage gain to triple. This lax gain control is generally unacceptable because it usually wastes most of the received power in the voltage regulation.

FIG. 2A is a schematic of the transmitter and receiver elements of an inductive link ($L_t$ and $L_r$), the tuning elements ($\omega_r = 1/\sqrt{L_r C_r}$ and $\omega_t = 1/\sqrt{L_t C_t}$, the transmitter loss and receiver load elements ($R_t$ and $R_r$) and the transmitter source and receiver voltages. This circuit reduces the coupling dependent gain variation by tuning the coils to two different frequencies; one above and one below the operating frequency. If these coils' resonances are placed optimally, their effective poles will shift as the mutual coupling of the coils changes. The gain will be compensated as a result.

Figure 3A:
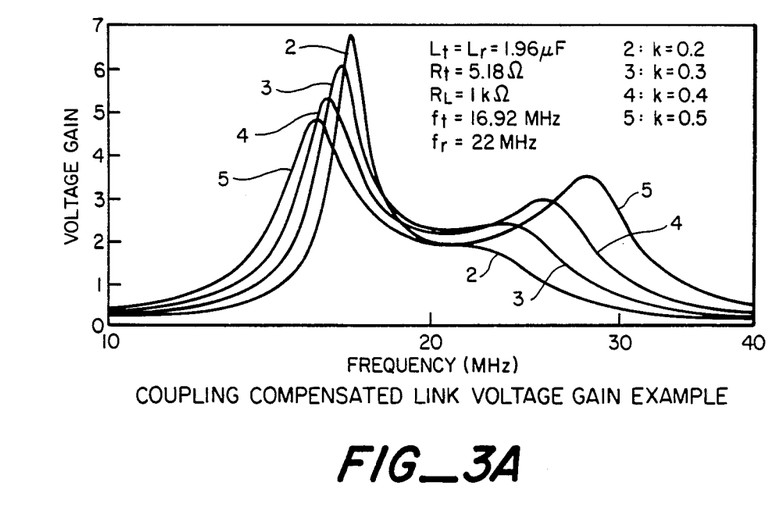
FIGS. 3A to 3C illustrates the effective result of a coupling compensated link voltage device using the circuit combination shown in FIG. 2A.

The "voltage driven:voltage out" link will help illustrate the new approach to gain control. FIG. 3A is a plot of the voltage gain versus frequency and coupling for a link that was designed to operate at 20 MHz. The numbers on the curves represent the values of coupling coefficient; 2 means $\kappa = 0.2$, 3 means $\kappa = 0.3$, and so on. The link is stagger-tuned; i.e., the component values are selected as shown so that one pole is placed above the operating frequency and one below, so the poles move as the coupling coefficient changes. If they are placed properly, their positions move to compensate for the changing coupling. To illustrate, in FIG. 3A as the coupling increases, the poles move away from the operating frequency. Increased coupling would normally raise the gain at 20 MHz, but the higher coupling has moved the poles away from the 20 MHz operating frequency, therefore lowering the gain at the operating frequency. The net result, for this example, is that even though the coupling coefficient changes by 250%, the gain changes by less that ±10%.

Since this approach is based on coupling, not geometry, it not only corrects for lateral displacement and tilt, as did the prior art geometric approach, but it also handles coil separation, which the geometric solution did not.

Also notice that the gain changes smoothly around the operating frequency (20 MHz), giving a stable gain over a relatively large frequency band. Classically, stagger tuning has been used to increase the bandwidth of a system without excessively loading the tuned circuits. As the example of FIG. 3A shows, the new approach to gain control has carried over the attractive feature of a wide bandwidth. For many applications, the additional bandwidth can simplify the design. For example, power and data links are combined into one inductive link by sending power on the carrier and the data by frequency-modulating (FM) the carrier as discussed in the application of Galbraith, et al. now U.S. Pat. No. 4,592,359 filed concurrently herewith and entitled, An Eight Channel Implantable Neural Stimulator," incorporated herein by reference.

This example has clearly demonstrated a wide link gain which is coupling-insensitive. With these capabilities, the power lost across the internal voltage regulators of an implanted stimulator can be reduced by taking advantage of the stable gain. By using equal sized coils, instead of the mismatched coil sizes of the geometric approach, the average coupling can be improved which lowers the transmitter coil $I^2R$ losses. The coupling-compensated link not only allows improved efficiency, but it also provides a large bandwidth, something that the previous approaches have sacrificed for efficiency.

To take advantage of the efficiency afforded by the stagger-tuned link's stable gain, the link needs a transmitter that can efficiently handle a variable load impedance while maintaining a constant driving voltage or current. Semi-passive drivers, such as class C or class E, are not paractical because they lose efficiency if the load impedance is not resonant at the operating frequency, a fundamental incompatibility with stagger tuning. A class D transmitter, on the other hand, can drive these loads efficiently, and can supply a constant driving source so that the link output voltage, or current, remains stable.

A class D transmitter, can drive these loads efficiently, because it can supply a constant source which is independent of the load. It simply switches the input of the link between the two terminals of the power supply. Reactive loads and load variations, due to changing coupling, should not affect its output level.

This driver also has a theoretical maximum efficiency of 100%, meaning that its efficiency is not bounded by a sub-optimum theoretical limit, an advantage in any design. The driver's loss is proportional to the ratio of the voltage dropped across its switches to the supply voltage. It is fairly simple to make this ratio quite small, and in practice, the design tends to become more efficient as the output power level is raised. In fact, the efficiency improves when it is needed most, when the transmitter is delivering the maximum power. The class D driver, therefore, meets the requirements for driving the stagger tuned link; it can efficiently drive a variable load with a stable source.

Figure 4:
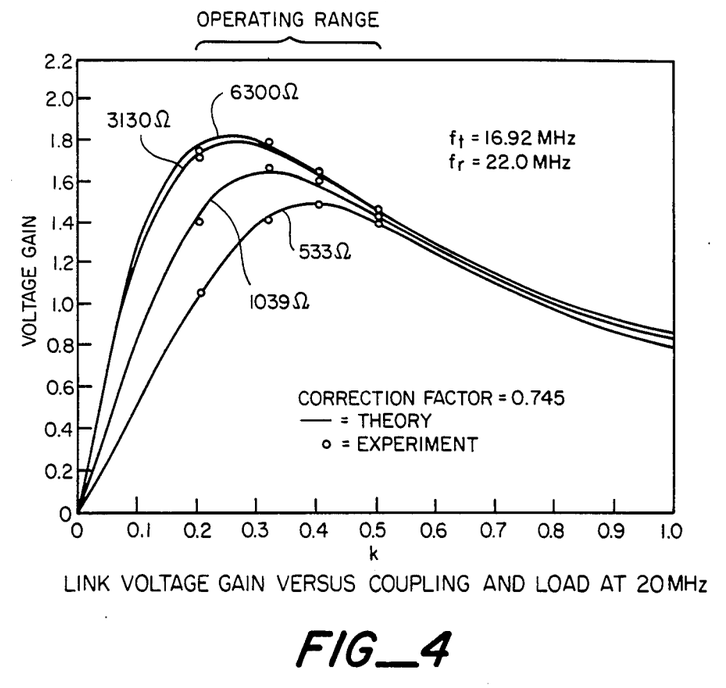
FIG. 4 is a second graph illustrating the effective relationship of gain versus coupling and load impedance at a given operating frequency of 20 MHz.

A class D driver has another advantage due to its square wave output. The Fourier Series of a square wave has a fundamental sine wave whose amplitude is $4/\pi$ times the amplitude of the square wave. The stagger tuned link passes the fundamental and attenuates the harmonics, meaning that the class D driver provides the added advantage of another 27% increase in gain. Other design considerations may trade off this additional gain to further advantage. For example, FIG. 4 shows the theoretical and experimental gain versus coupling for the 20 MHz link described above. It has a correction factor of 0.745 which means that the theoretical gain is multiplied by 0.745 to match the experimental results. The difference between theory and practice comes from operating the coils near their self-resonant frequencies. The parasitic capacitance of the transmitter coil acts with the tuning capacitance to form a voltage divider between the transmitter and the inductor. It lowers the amount of voltage reaching the tuned circuit. In this example, the additional square wave gain (27%) was used to replenish the gain lost to the self resonance. A typical class D driver usable with the coils described above is shown in FIG. 5.

Now that the concept behind the gain control and its drive requirements have been described, and examples shown, it is appropriate to discuss a design procedure, including some of the design tradeoffs.

The following procedure was used to create a stagger tuned power and data link; a "voltage driven:voltage out" link. The goals for this procedure were:

(1) to minimize the variation in output voltage, due to changing load and coupling, over a band of frequencies;

(2) to keep a reasonably high input impedance so a transmitter would not need to supply excessively large driving currents;

(3) to make the input impedance inductive so that a class D voltage driver would switch cleanly; and (4) to exceed a minimum required voltage gain.

This procedure initially determines whether a design is feasible. If so, then it uses an iterative process to meet the design goals.

The procedure begins by specifying the type of link, coupling range, load range, and operating frequency. These choices may be limited by size constraints, FCC regulations, or power requirements. The equation below is an approximation which applies to all of the link combinations. It gives the ratio of the magnitude of the minimum gain to the maximum gain (G) in terms of a ratio of the minimum and maximum coupling coefficients ($\kappa_{min}$ and $\kappa_{max}$). Note that $0 \leftarrow \kappa_{min} \leftarrow \kappa_{max} \leftarrow$ and $0 \leftarrow G \leftarrow 1$.

$$G = \frac{|gain_{min}|}{|gain_{max}|} \simeq \frac{2\sqrt{\kappa_{max}/\kappa_{min}}}{1 + \kappa_{max}/\kappa_{min}}$$

The coupling range ($\kappa_{min}$ and $\kappa_{max}$) is usually found experimentally. If the gain variation is too large (G is too small), then the coupling range needs to be reduced (preferably by raising the minimum value of coupling which has the added advantages of lowering the transmitter coil losses by reducing the transmitter current, and also improving the load insensitivity of the gain by lowering the link output impedance). One possible solution is to use larger coil diameters. A larger diameter will reduce the coupling range as long as the alignment tolerance is held constant. Another solution is to use a ferrite backing on either or both coils. The ferrite will compress the magnetic field around the coils and raise their mutual coupling.

Since the gain is still somewhat dependent on coupling, it is necessary to find the values of coupling which produce the minimum and maximum values of gain. The minimum gain occurs, by design, at the minimum and maximum values of coupling ($\kappa_{min}$ and $\kappa_{max}$). The maximum gain occurs at the optimum value of coupling given by equation $K_{opt} = K_{min} K_{max}$ From here on, the procedure tends to be iterative. Next, the minimum inductance of each of the two coils is chosen. The receiver coil inductance must provide a reasonable Q (for example, greater than 10) for the loaded receiver tank circuit. If the Q is too low, the output voltage will be sensitive to changes in the load. Also, to maintain a reasonable overall efficiency, the transmitter coil inductance should provide a large enough input impedance so that the transmitter will not have to supply an excessive current into the link (generally, raising the transmitter coil's inductance raises the link's input impedance).

The next step is to set the minimum gain and reduce the gain variation over a band of frequencies. A ratio of receiver resonance to the operating frequency ($\omega_r/\omega$) is chosen. (Remember, if the link is driven by a class D transmitter, ($\omega_r/\omega$) should be chosen so that the input impedance looks inductive, which allows the transmitter to provide efficient switching.) This ratio along with the resistances, coupling range and coil inductances, fixes the ratio of the transmitter resonance to the operating frequency ($\omega_t/\omega$). The equations which specify $\omega_t/\omega$ are different for each type of link and are given below.

Next, plots are made of the gain versus frequency for the six combinations of minimum and maximum load ($R_{min}, R_{max}$); and minimum, optimum, and maximum values of coupling ($k_{min}, K_{opt}, K_{max}$). The required gain is obtained by varying the turns ratio (inductance of the coils and adjusting $\omega_r/\omega$. For example, if the gain is too small, then the turns ratio should be changed or $\omega_r/\omega$ moved closure to unity. If the gain variation, due to loading, is too large over the frequency band, then the receiver coil Q should be increased. If the spread is lop-sided (more variation on one side of the band than on the other), then $\omega_r/\omega$ needs to be slightly adjusted until the gain is acceptably uniform about the operating frequency.

There are four combinations of link gain; voltage gain, current gain, transconductance gain, and transimpedance gain. The link gain equation for all four combinations has the form $$F(\kappa) = \frac{A\kappa}{(B\kappa^2 + C) + j(D\kappa^2 + E)}$$

where k is the coupling coefficient ($0 \leftarrow \kappa \leftarrow 1$), and A, B, C, D, and E are variables dependent on the link combination.

$$f(k) = |F(k)| = \frac{Ak}{\sqrt{Xk^4 + yk^2 + z}} = \frac{(A/\sqrt{Z})k}{\sqrt{\left(\frac{X}{Z}\right)k^4 + \left(\frac{Y}{Z}\right)k^2 + 1}}$$

where
$X = B^2 + D^2$
$Y = 2BC + 2DE$
$Z = C^2 + E^2$

Summarizing for the general section: the minimum gain occurs at $k_{min}$ and $k_{max}$, while the maximum gain occurs at $$k_{opt} = \sqrt{k_{min}k_{max}}$$

and is given by $$f(k_{opt}) \simeq \frac{A}{2} \frac{\sqrt{k_{min}k_{max}}}{Z}$$

The ratio of the minimum gain to the maximum gain is $$G \simeq \frac{2\sqrt{\frac{k_{max}}{k_{min}}}}{1 + \frac{k_{max}}{k_{min}}}$$

Therefore, the amount of gain variation (G), and the coupling values where the minimum and maximum gains occur ($f_{min} = f(k_{min}) = f(k_{max})$, and $f_{max} = f(k_{opt})$) are known by simply specifying the coupling range.

Figure 2:
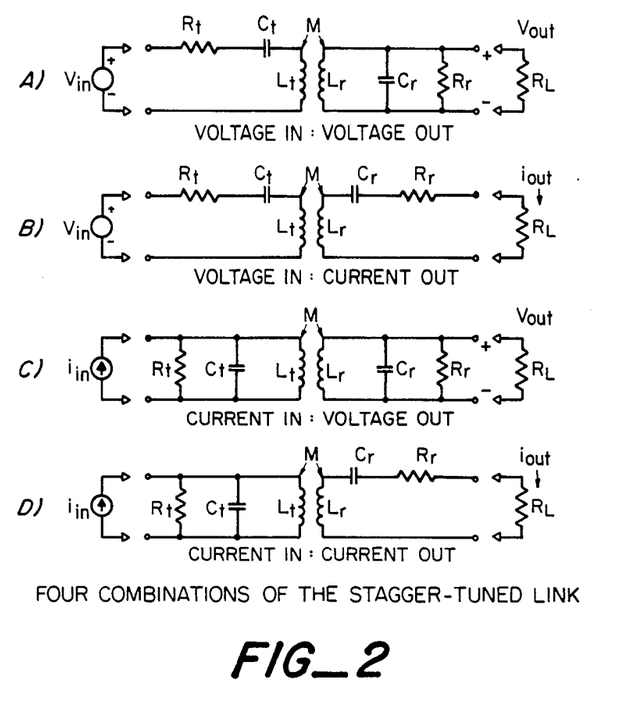
FIG. 2 shows the four possible combinations of stagger-tuned links.

FIG. 2, circuit A is a circuit diagram of a stagger-tuned link which is driven by a voltage source and whose output appears as a voltage source. This arrangement is the type used by the preferred embodiment. For this circuit the general parameters are $$A = -\frac{\omega^2}{\omega_t^2} \sqrt{\frac{L_r}{L_r}}$$

$$B = -\frac{\omega^4}{\omega_t^2 \omega_r^2}$$

$$C = \left(1 - \frac{\omega^2}{\omega_r^2}\right)\left(1 - \frac{\omega^2}{\omega_t^2}\right) - \frac{\omega^2}{\omega_t^2 Q_t Q_r}$$

$$D = \frac{\omega^2}{\omega_t^2 Q_r}$$

$$E = \frac{1}{Q_r}\left[1 - \frac{\omega^2}{\omega_t^2}\right] + \frac{1}{Q_t} \frac{\omega^2}{\omega_t^2}\left[1 - \frac{\omega^2}{\omega_r^2}\right]$$

$$\omega_t^2 = \frac{1}{L_t C_t}$$

$$\omega_r^2 = \frac{1}{L_r C_r}$$

$$Q_t = \frac{\omega L_t}{R_t}$$

$$Q_r = \frac{R_r}{\omega L_r}$$

Note that $\kappa_{opt}^4 = Z/X = (C^2 + E^2)/(B^2 + D^2)$. So substituting and simplifying give $$k_{opt}^4 = \frac{\left[\left(1 - \frac{\omega^2}{\omega_t^2}\right)^2 + \left(\frac{1}{Q_t} \frac{\omega^2}{\omega_t^2}\right)^2\right]\left[\left(1 - \frac{\omega^2}{\omega_r^2}\right)^2 + \frac{1}{Q_r^2}\right]}{\left(\frac{\omega^2}{\omega_t^2}\right)^2 \left[\left(\frac{\omega^2}{\omega_r^2}\right)^2 + \frac{1}{Q_r^2}\right]}$$

Solving for the ratio of the operating frequency to the transmitter resonance $\omega^2/\omega_t^2$ and simplifying gives $$\frac{\omega^2}{\omega_t^2} = \frac{1 \pm \sqrt{H - 1/Q_t^2}}{1 - H + 1/Q_t^2}$$

where $$H = \frac{k_{opt}^4 \left[\left(\frac{\omega^2}{\omega_r^2}\right)^2 + \frac{1}{Q_r^2}\right]}{\left(1 - \frac{\omega^2}{\omega_r^2}\right)^2 + \frac{1}{Q_r^2}}$$

Note the one restriction $$Q_t \geq \frac{1}{\sqrt{H}}$$

Therefore, given the minimum and maximum coupling coefficient, the coil Q's, the operating frequency, and the resonant frequency of the receiver, equation gives the transmitter resonance that minimizes the sensitivity of the gain to the coupling variations. The other three possible stagger-tuned links shown in FIGS. 2B, 2C, 2D follow an equivalent approach.

Further details of an exemplary embodiment will be given below.

link type: "voltage driven: voltage out"
   coupling range: $0.2 \leq \kappa \leq 0.5$
   load range: $1k\Omega \geq R \geq 3k\Omega$
   operating frequency: 20 MHz
   frequency range: $19\ MHz \leq f \leq 21\ MHz$
   transmitter type: class D voltage source
   acceptable gain variation across the bandwidth, including the load variation: 0.5 drop from the maximum
   minimum gain: $\simeq 2.0$ The ratio of minimum to maximum voltage gain is approximately 0.90, which is well within the goal of 0.5. Next, two identical coils, with ferrite backings for high coupling, are chosen. They are 1.96 $\mu$h with a series resistance of 5.8$\omega$ at 20 MHz. These numbers give a transmitter tank Q of about 40 and a receiver tank Q, including the 1k$\Omega$ load, of about four.

Next $\omega_r/\omega$ is chosen greater than one so that the input appears inductive for the class D transmitter. Let $\omega_r/\omega = 1.1$.

Figure 3B:
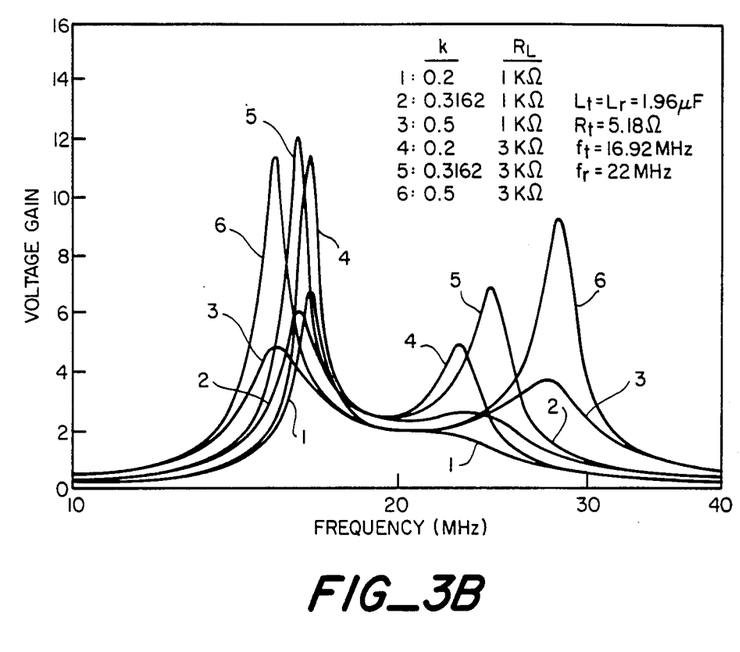

FIG. 3B is a plot of the gain versus frequency for the six combinations of coupling and load, using the equations in the appendix for a "voltage driven: voltage out" link.

Figure 3C:
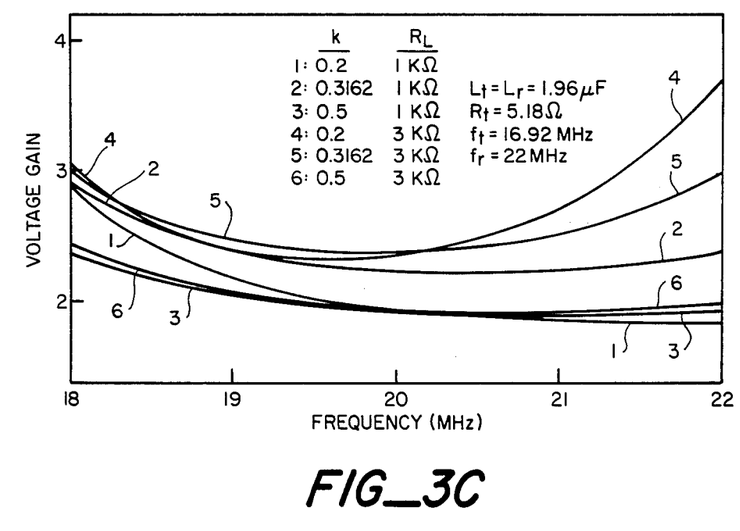

FIG. 3C is an expanded view of the gain around the operating frequency (20 MHz). The maximum gain deviation occurs at the high end of the frequency range (21 MHz). The ratio of minimum to maximum gain is 0.7 which exceeds the design goal of 0.5. The minimum gain is about 1.9 which is only 5% below the goal of 2, well within the tolerances of most components, and probably acceptable.

Remember that the receiver Q was rather low, only 4. The dependence of the output voltage on the load is the result of a voltage division between the link output impedance and the effective load impedance. If the link impedance is significant compared to the load, then the output voltage will be load dependent. The curves labeled 1 and 4 on FIG. 3C illustrate this point. These curves represent the gain for the minimum and maximum loads at the lowest value of coupling. This link has its highest output impedance when the coils are coupling the least. Over the design band (19 MHz–21 MHz), the largest gain spread occurs at 21 MHz and is bounded by curves 1 and 4. Here, the output impedance of the link (equivalent to about 800 ohms) is significant compared to the load, so the output voltage is somewhat load sensitive. Two ways of reducing the output impedance are: one, raise the coupling coefficient (use ferrite backings and larger coil diameters); and two, make sure that the Q of the loaded receiver coil is reasonably high (adjust the receiver coil inductance).

Figure 5:
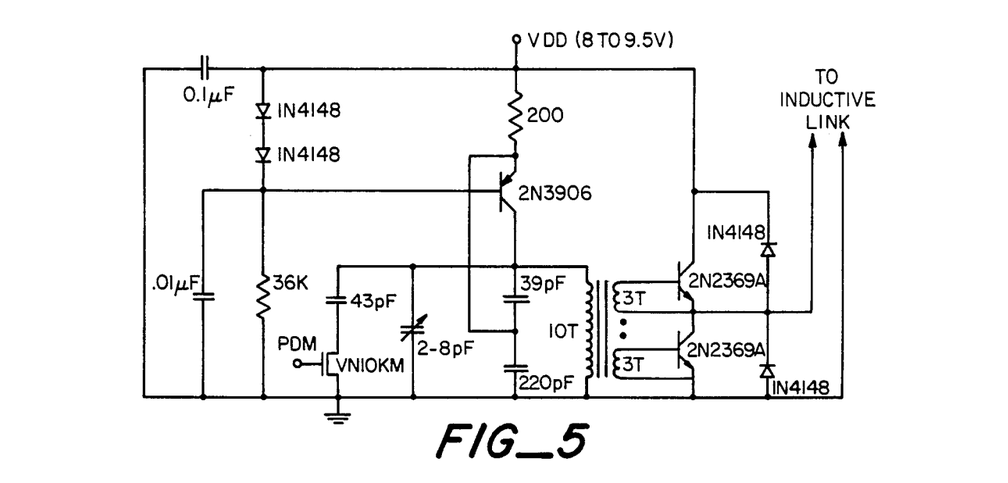
FIG. 5 is a detailed schematic of a Class D transmitter useful in driving the link of the present invention.

As mentioned before, this link places some requirements on the driver. FIG. 5 shows a preferred embodiment of a transmitter design used to drive the link. This circuit is a class D FM voltage driver with several features for portable, efficient operation. Its frequency is fairly insensitive to changes in the power supply voltage, so that it can operate from transistor radio batteries without regulation. Its frequency deviation is controlled by a CMOS compatible input which interfaces easily to portable digital logic. It also uses core drivers in the output stage to rapidly and efficiently switch the high output currents.

The stagger-tuned link, in this example, has a minimum input impedance of about 47$\Omega$, a fairly small load for the transmitter to drive. An efficiency of 35% allows the link to operate for a full day (16 hours) on two nine volt transistor radio batteries. This efficiency provides a major reduction in power consumption and battery size over previous Stanford stimulators (a worst case power consumption of 140 mW instead of 400 mW, and two nine volt batteries instead of a brick-sized battery pack).

The link receives its power from an RF carrier sent across the inductive link, and extracts its data from a frequency-modulation (FM) of this carrier. This approach decouples the information from the output voltage, again keeping the output voltage fairly constant for the sake of efficiency. But FM requires a wider bandwidth than that needed for just the data. This link provides that additional bandwidth. This link is still capable of delivering a base-band data rate of one megabit per second. This data rate is very high for a neural stimulator. In fact, the band-width limiting element of the Stanford Stimulator this stimulator system was not the link, but the FM receiver (due to transistors with only a 20 MHz beta cutoff frequency). The stagger-tuned link can provide both a large bandwidth and a high efficiency; two characteristics which were mutually exclusive in previous links.

Figure 6:
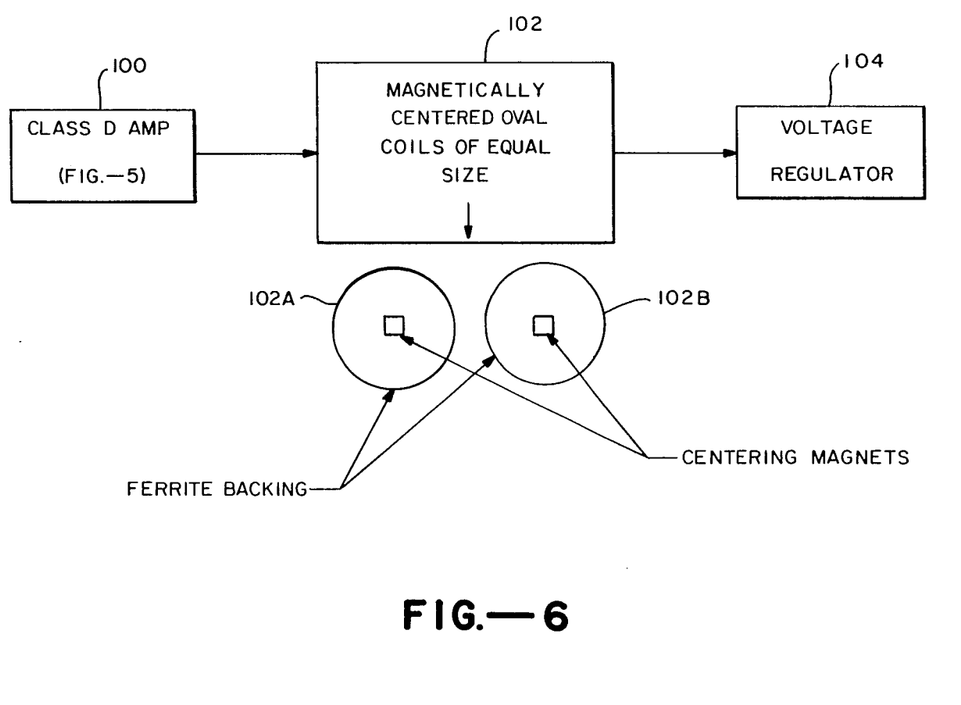
FIG. 6 is a block diagram of the basic elements of the invention.

FIG. 6 is a block diagram of the basic elements of a preferred embodiment of the system, comprising a class D amplifier 100 driving a pair of magnetically centered coils 102. The coils, shown as coils 102A, B, preferably have ferrite backing and are kept centered by magnets carried in the coil centers. The output of the coils is through a voltage regulator 104.

Inductive links provide a safe means of delivering both power and data into devices implanted in the body. With the appropriate applications of stagger tuning, these links can now provide a high efficiency by taking advantage of a coupling desensitized link gain. They can also supply a large bandwidth without adversely effecting their efficiency. This technique is successful in neural stimulators and can easily be applied to many other applications requiring coupling insensitivity.

What is claimed:

1. An inductive link for conveying power and/or data through the skin of a user comprising a first external coil, a second medically implantable coil, the coils being movable relative to one another, the mutual inductive coupling of said coils changing with their position relative to one another, and a means for stagger tuning said first and second coils to maintain a gain which is relatively independent of the coil's mutual coupling at a selected frequency or frequency band of interest.

2. An inductive link as in claim 1 further comprising a class D transmitter means coupled to said first coil for driving said first externally mounted coil.

3. An inductive link as claimed in claim 1 further comprising a voltage regulator coupled across the terminals of said second implanted coil.

4. An inductive link as claimed in claim 1 wherein said coils are circular and of equal size.

5. An inductive link as in claim 4 wherein each of said coils includes a magnet substantially in the center of said coil, the magnets having opposite poles aligned for maintaining alignment of the coils.

6. An inductive data link as in claim 1 wherein each of said means for stagger tuning comprise an RC network, each of said RC networks comprising a filter, the values of each of said RC network components being selected to tune one of said coils above the frequency of interest, the other of said coils being tuned below the frequency of interest.

7. An inductive link as in claim 6 wherein said means for stagger tuning comprise a series RC network coupled in series with said first input coil and a parallel RC output network coupled in parallel with said second coil to define a voltage in: voltage out relationship.

8. An inductive link as in claim 7 further comprising a voltage regulator coupled across the terminals of said second implanted coil.

9. An inductive link as in claim 6 wherein said means for stagger tuning comprise a parallel RC network coupled in parallel with said first coil and a parallel RC network coupled in parallel with said second coil to define a current in: voltage out relationship.

10. An inductive link as in claim 9 further comprising a voltage regulator coupled across the terminals of said second implanted coil.

11. An inductive link as in claim 6 wherein said means for stagger tuning comprise a series RC network coupled in series with said first coil and a series RC network coupled in series with said second coil to define a voltage in: current out relationship.

12. An inductive link as in claim 6 wherein said means for stagger tuning comprise a parallel RC network coupled in parallel with said first coil and a series RC network coupled in series with said second coil to define a current in: current out relationship.

13. An inductive link as in claim 7, 9, 11, 12, 8 or 10 comprising an FM transmitter means for driving said first coil for transferring power and data to said second coil.

14. An inductive link as in claim 1 including ferrite backing on said first and second coils to maximize increase coupling between said coils.

* * * * *

UNITED STATES PATENT AND TRADEMARK OFFICE
CERTIFICATE OF CORRECTION

PATENT NO. : 4,679,560

DATED : July 14, 1987

INVENTOR(S) : Douglas C. Galbraith

It is certified that error appears in the above-identified patent and that said Letters Patent is hereby corrected as shown below:

Column 1, line 5, insert the following paragraph:

--The U.S. Government has rights to this invention under Contract N01-NS-1-2354 and N01-NS-5-2306 awarded by the National Institutes of Health to Stanford University.--

Signed and Sealed this

Twenty-second Day of May, 1990

Attest:

HARRY F. MANBECK, JR.

*Attesting Officer*     *Commissioner of Patents and Trademarks*